United States Patent [19]

Baldwin et al.

[11] Patent Number: 4,677,102
[45] Date of Patent: Jun. 30, 1987

[54] SUBSTITUTED DIAZAPINES AND DERIVATIVES THEREOF USEFUL IN THE TREATMENT OF CARDIOVASCULAR DISORDERS

[75] Inventors: John J. Baldwin, Gwynedd Valley; David E. McClure, Lansdale; David A. Claremon, Audubon, all of Pa.

[73] Assignee: Merck & Co., Inc., Rahway, N.J.

[21] Appl. No.: 827,035

[22] Filed: Feb. 7, 1986

[51] Int. Cl.[4] .................... C07D 243/04; A61K 31/55
[52] U.S. Cl. .................................... 514/218; 540/492
[58] Field of Search ......................... 540/492; 514/218

[56] References Cited

PUBLICATIONS

Bullock et al., "Can. J. Chem.", vol. 55, (1977) pp. 895–905.
Ashby et al., "J.C.S. Perkin I" (1975) pp. 657–662.

*Primary Examiner*—Robert T. Bond
*Attorney, Agent, or Firm*—Salvatore C. Mitri; Michael C. Sudol; Mario A. Monaco

[57] ABSTRACT

There are disclosed novel diazapines and derivatives thereof which are useful in the treatment of cardiovascular disorders.

14 Claims, No Drawings

SUBSTITUTED DIAZAPINES AND DERIVATIVES THEREOF USEFUL IN THE TREATMENT OF CARDIOVASCULAR DISORDERS

BACKGROUND OF THE INVENTION

Substituted dihydropyridines are known to be useful for reducing blood pressure, effecting dilation of the coronary vessels, and preventing vasospasms. Typical of such substituted dihydropyridines are those disclosed in U.S. Pat. Nos. 3,923,818; 3,905,970; 4,044,141; 4,237,137; and 4,285,955.

SUMMARY OF THE INVENTION

This invention is directed to novel substituted diazepines and derivatives thereof which are useful in the treatment of certain cardiovascular disorders.

DETAILED DECRIPTION OF THE INVENTION

The novel substituted diazepines of this invention are represented by the following general structural formula (I):

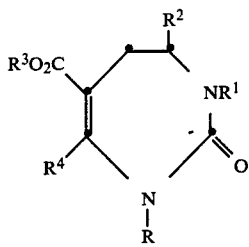

I wherein:
R is hydrogen or COY wherein Y is $C_1$–$C_8$alkyl;
$R^1$ is hydrogen;
  $C_1$–$C_8$alkyl;
  COX wherein X is $C_1$–$C_8$alkyl, $C_2$–$C_8$alkenyl, $C_3$–$C_8$cycloalkyl, phenyl, $C_1$–$C_8$alkoxy, $C_2$–$C_8$alkenyloxy, $C_3$–$C_8$cycloalkyloxy or $NR^5R^6$ wherein $R^5$ and $R^6$ independently are hydrogen, $C_1$–$C_8$alkyl, $C_7$–$C_{14}$phenylalkyl or $R^5$ and $R^6$ together with the N atom form a 5 or 6 membered heterocycle containing up to four heteroatoms selected from O, S or N;
$R^2$ and $R^4$ independently are hydrogen;
  $C_1$–$C_8$alkyl;
  aryl of 6 to 10 carbon atoms;
  substituted aryl of 6 or 10 atoms containing up to five substituents selected from $C_1$–$C_8$alkyl, $C_1$–$C_8$alkoxy, $C_1$–$C_8$alkylthio, $C_1$–$C_8$alkyl S(O), $C_1$–$C_8$alkyl S(O)$_2$, CF$_3$, halo (Br, Cl, F), CHF$_2$ or CONR$^5$R$^6$, wherein $R^5$ and $R^6$ are as defined above;
  benzoxadiazole;
  heteroaryl of 5 or 6 atoms containing up to four heteroatoms selected from O, S or N;
  substituted heteroaryl of 5 or 6 atoms containing up to three substituents selected from CF$_3$, and $C_1$–$C_8$alkylthio;
  provided that $R^2$ and $R^4$ are not both hydrogen and when $R^2$ is hydrogen, $R^4$ is not alkyl;
$R^3$ is $C_1$–$C_8$alkyl;
  $C_3$–$C_8$cycloalkyl;
  $C_1$–$C_8$hydroxyalkyl;
  $C_1$–$C_8$dihydroxyalkyl;
  $C_1$–$C_8$aminoalkyl wherein the amino group is $NR^5R^6$ in which $R^5$ and $R^6$ are as defined above;
and, pharmaceutically acceptable salts thereof.

The preferred compounds of this invention are those represented by the general structural formula (I) wherein
R is hydrogen;
$R^1$ is hydrogen, $C_1$–$C_8$alkyl or COX wherein X is $C_1$–$C_8$alkyl, $C_1$–$C_8$alkoxy or phenyl;
$R^2$ and $R^4$ independently are hydrogen;
  $C_1$–$C_8$alkyl;
  aryl of 6 to 10 carbon atoms;
  substituted aryl of 6 or 10 atoms containing up to five substituents selected from $C_1$–$C_8$alkyl, $C_1$–$C_8$alkoxy, $C_1$–$C_8$alkylthio, $C_1$–$C_8$alkyl S(O), $C_1$–$C_8$alkyl S(O)$_2$, CF$_3$, halo (Br, Cl, F), CHF$_2$ or CONR$^5$R$^6$, wherein $R^5$ and $R^6$ are as defined above,
  benzoxadiazole;
  heteroaryl of 5 or 6 atoms containing up to four heteroatoms selected from O, S or N;
  substituted heteroaryl of 5 or 6 atoms containing up to three substituents selected from CF$_3$, and $C_1$–$C_8$alkylthio;
  provided that $R^2$ and $R^4$ are not both hydrogen and when $R^2$ is hydrogen, $R^4$ is not alkyl;
$R^3$ is $C_1$–$C_8$alkyl, $C_1$–$C_8$aminoalkyl wherein the amino group is $NR^5R^6$ in which $R^5$ and $R^6$ are as defined above.

The most preferred compounds of this invention are those represented by the general structural formule (I) wherein
R is hydrogen;
$R^1$ is hydrogen or COY wherein Y is $C_1$–$C_8$alkyl, $C_1$–$C_8$alkoxy or phenyl;
$R^2$ is aryl of 6 carbon atoms;
  substituted aryl of 6 carbon atoms wherein the substituents are $C_1$–$C_8$alkoxy, trifluoromethyl, and, pentafluoro;
  pyridyl;
  naphthyl;
$R^3$ is $C_1$–$C_8$alkyl or

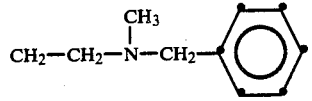

$R^4$ is $C_1$–$C_8$alkyl or aryl of 6 carbon atoms.
Illustrative of the most preferred compounds are the following:

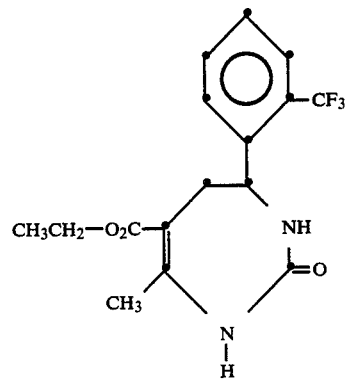

(1)

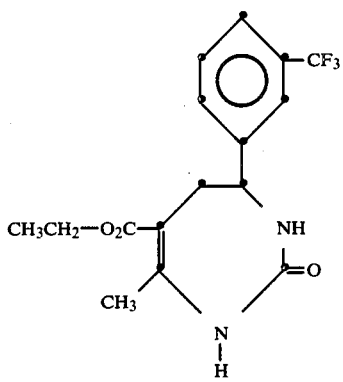

(2)

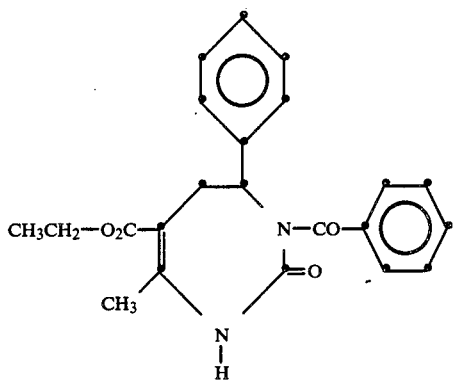

(3)

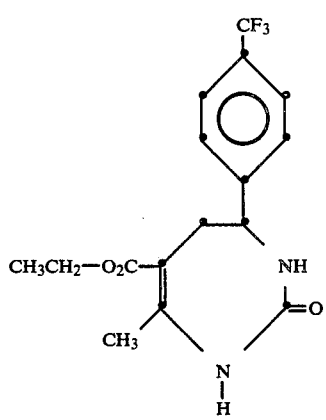

(4)

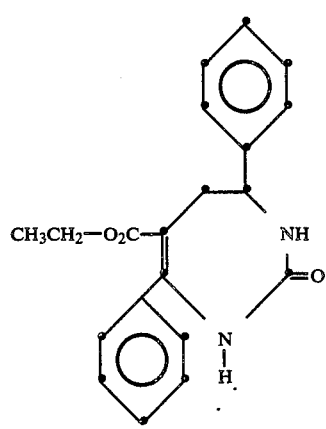

(5)

(6)

As indicated above, the compounds of this invention are useful in the treatment of cardiovascular disorders and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipidemic action; (vii) protection of the ischemic myocardium; (viii) inhibition of irritable bowel syndrome and esophageal spasm; and, (ix) inhibition of migraine. Some of these compounds are also useful cardiotonic agents.

Representative compounds of the present invention were found to inhibit vascular calcium contraction, reduce cardiac contractile force, inhibit calcium-mediated tracheal contraction, inhibit calcium uptake in pituitary cells, or displace tritiated nitrendipine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified. The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or B-blocking agents, and/or cardiotonic agents. For example, the compounds of this invention can be given in combination with such compounds as enalapril, hydralazine hydrochloride, hydrochlorothiazide, methyldopa, timolol, digitalis and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The compounds of the invention can be prepared according to the following Reaction Scheme wherein $R-R^4$ are as defined above unless otherwise indicated.

REACTION SCHEME

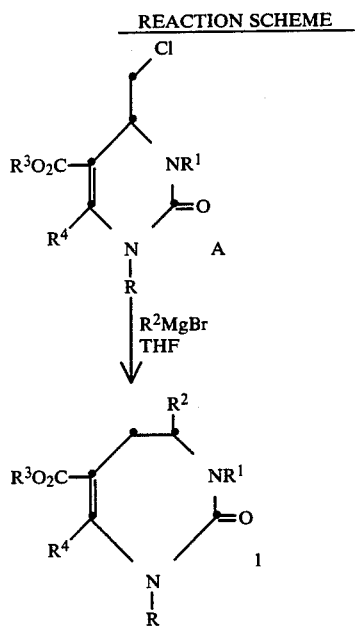

In the foregoing Reaction Scheme, starting compounds A can be obtained using the methods described by J. Ashley, et al., *J. Chem. Soc. Perk. I*, 657 (1975).

Under an inert atmosphere (e.g., argon) and using standard anhydrous techniques, starting compound A (10 mmol) is suspended in tetrahydrofuran (THF) (20 ml), stirred at $-78°$ C., and treated dropwise with phenylmagnesium bromide (3.0M in ether, 10.7 ml, 32 mmol) or other typical Grignard reagent. After the addition of the phenyl-magnesium bromide is complete, the cooling bath is removed and the reaction is followed by TLC (silica gel). When the reaction is complete, ca. 15 minutes at $23°$ C., the excess Grignard reagent is quenched with saturated aqueous $NH_4Cl$. Extraction with chloroform, drying over $MgSO_4$, filtration and concentration at reduced pressure (15 mmHG) affords compounds 1 which are homogeneous by TLC (silica gel, 1% methanol in ether) as white solids which are either washed with cold anhydrous ether or recrystallized from ethyl acetate/hexanes to afford compounds 1 of the invention.

To obtain compounds 1 where $R^1 \neq H$, one can treat compounds 1 where $R^1 = H$ with 2 molar equivalents of an alkyl organometellic such as methyl lithium or methyl magnesium chloride in THF at $-78°$ C. and quenching with an alkanoyl halide or alkoxy carbonyl halide such as acetyl chloride or methyl chloroformate followed by normal extraction procedures to recover the desired product.

EXAMPLES 1a–1n

Following the procedures described for the Reaction Scheme above, illustrative compounds of the invention were obtained. These illustrative compounds are shown in Table I below.

TABLE 1

COMPOUNDS OF EXAMPLES 1a-1n

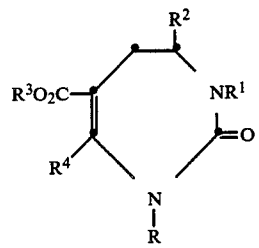

| Compound of Example | R | $R^1$ | $R^2$ | $R^3$ | $R^4$ |
|---|---|---|---|---|---|
| 1a | H | H | 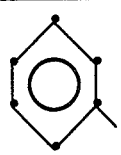 | $CH_3CH_2$ | $CH_3$ |

TABLE 1-continued
COMPOUNDS OF EXAMPLES 1a-1n
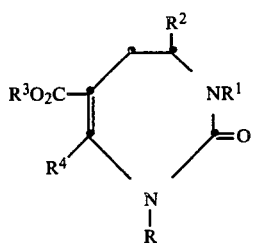
| Compound of Example | R | R¹ | R² | R³ | R⁴ |
|---|---|---|---|---|---|
| 1b | H | H | ⌬-OCH₃ (para) | CH₃CH₂ | CH₃ |
| 1c | H | H | F₃C-⌬ | CH₃CH₂ | CH₃ |
| 1d | H | H | CF₃-⌬ (ortho) | CH₃CH₂ | CH₃ |
| 1e | H | H | ⌬-CF₃ (meta) | CH₃CH₂ | CH₃ |
| 1f | H | H | pentafluorophenyl | CH₃CH₂ | CH₃ |
| 1g | H | H | ⌬ | CH₃CH₂ | ⌬ |
| 1h | H | H | CH₃ | CH₃CH₂ | ⌬ |

TABLE 1-continued
COMPOUNDS OF EXAMPLES 1a-1n

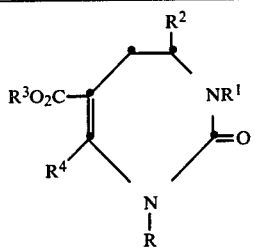

| Compound of Example | R | $R^1$ | $R^2$ | $R^3$ | $R^4$ |
|---|---|---|---|---|---|
| 1i | H | —CO—C₆H₅ | C₆H₄— | $CH_3CH_2$ | $CH_3$ |
| 1j | H | —$CO_2CH_3$ | C₆H₄— | $CH_3CH_2$ | $CH_3$ |
| 1k | H | —$COCH_3$ | C₆H₄— | $CH_3CH_2$ | $CH_3$ |
| 1l | H | H | H | $CH_3CH_2$ | C₆H₄— |
| 1m | $CO_2CH_3$ | $CO_2CH_3$ | C₆H₄— | $CH_3CH_2$ | $CH_3$ |
| 1n | $CO_2CH_3$ | H | C₆H₄— | $CH_3CH_2$ | $CH_3$ |

The yield, physical and chemical properties, and analytical data for the compounds of Examples 1a–1h are set forth in Table II below wherein "IR(nujol)" denotes infrared solvent and " ∼∼[CM$^{-1}$]" denotes physical measurements from the Infrared spectrum; "TMS" is tetramethylsilane; and, "[PPM]" denotes parts per million for NMR spectral properties:

TABLE II
PHYSICAL AND CHEMICAL PROPERTIES AND ANALYTICAL DATA FOR SELECTED COMPOUNDS OF EXAMPLES 1a-1n

| Compound of Example | Yield (%) | m.p. (°C.) | IR(nujol) ∼∼ [CM$^{-1}$] |
|---|---|---|---|
| 1a | 91 | 192–193.5 | 3290, 3190, 1670, 1645, 1610 |
| 1b | 87 | 189–190 | 3360, 3240, 1695, 1630, 1620 |
| 1c | 83 | 165–167 | 3380, 3240, 1700, 1680, 1630 |

TABLE II-continued

PHYSICAL AND CHEMICAL PROPERTIES AND
ANALYTICAL DATA FOR SELECTED COMPOUNDS
OF EXAMPLES 1a-1n

| Compound of Example | Yield (%) | m.p. (°C.) | IR(nujol) [CM$^{-1}$] |
|---|---|---|---|
| 1d | 85 | 175–177 | 3300, 3180, 1675, 1650, 1610 |
| 1e | 86 | 207–209 | 3360, 3249, 1695, 1675, 1720 |
| 1f | 76 | 254–255.5 | 3350, 3240, 1700, 1670, 1630 |
| 1g | 77 | 168–170 | 3240, 3100, 1695, 1680, 1630 |
| 1h | 74 | 131–134 | 3330, 3240, 1695, 1660, 1630 |
| 1i | 50 | 125–127.5 | |
| 1j | 90 | 224–225 | |
| 1k | 50 | 180–181.5 | |
| 1l | 30 | 158 | |
| 1m | 70 | oil | $^1$H NMR(CDCl$_3$) δ = 2.40(s,3H); 3.80(s,3H); 3.95(s,3H)ppm |
| 1n | 20 | 103–110 | |

What is claimed is:

1. A compound represented by the formula:

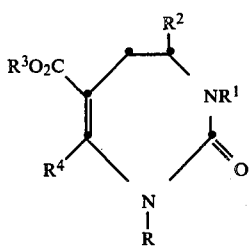

I wherein:
R is hydrogen or COY wherein Y is $C_1$-$C_8$alkyl;
$R^1$ is hydrogen;
  $C_1$-$C_8$alkyl;
  COX wherein X is $C_1$-$C_8$alkyl, $C_2$-$C_8$alkenyl, $C_3$-$C_8$cycloalkyl, phenyl, $C_1$-$C_8$alkoxy, $C_2$-$C_8$alkenyloxy, $C_3$-$C_8$cycloalkyloxy or $NR^5R^6$ wherein $R^5$ and $R^6$ independently are hydrogen, $C_1$-$C_8$alkyl, $C_7$-$C_{14}$phenylalkyl;
$R^2$ and $R^4$ independently are hydrogen;
  $C_1$-$C_8$alkyl;
  aryl of 6 to 10 carbon atoms;
  substituted aryl of 6 or 10 atoms containing up to five substituents selected from $C_1$-$C_8$alkyl, $C_1$-$C_8$alkoxy, $C_1$-$C_8$alkylthio, $C_1$-$C_8$alkyl S(O), $C_1$-$C_8$alkyl S(O)$_2$, $CF_3$, halo, $CHF_2$ or $CONR^5R^6$, wherein $R^5$ and $R^6$ are as defined above;
  benzoxadiazole;
  provided that $R^2$ and $R^4$ are not both hydrogen and when $R^2$ is hydrogen, $R^4$ is not alkyl;
$R^3$ is $C_1$-$C_8$alkyl;
  $C_3$-$C_8$cycloalkyl;
  $C_1$-$C_8$hydroxyalkyl;
  $C_1$-$C_8$dihydroxyalkyl;
  $C_1$-$C_8$aminoalkyl wherein the amino group is $NR^5R^6$ in which $R^5$ and $R^6$ are as defined above;
and, pharmaceutically acceptable salts thereof.

2. A compound of claim 1 wherein
R is hydrogen;
$R^1$ is hydrogen, $C_1$-$C_8$alkyl or COX wherein X is $C_1$-$C_8$alkyl, $C_1$-$C_8$alkoxy or phenyl;
$R^2$ and $R^4$ independently are hydrogen;
  $C_1$-$C_8$alkyl;
  aryl of 6 to 10 carbon atoms;
  substituted aryl of 6 or 10 atoms containing up to five substituents selected from $C_1$-$C_8$alkyl, $C_1$-$C_8$alkoxy, $C_1$-$C_8$alkylthio, $C_1$-$C_8$alkyl S(O), $C_1$-$C_8$alkyl S(O)$_2$, $CF_3$, halo, $CHF_2$ or $CONR^5R^6$, wherein $R^5$ and $R^6$ are as defined above;
  benzoxadiazole;
  provided that $R^2$ and $R^4$ are not both hydrogen and when $R^2$ is hydrogen, $R^4$ is not alkyl; and
$R^3$ is $C_1$-$C_8$alkyl, $C_1$-$C_8$aminoalkyl wherein the amino group is $NR^5R^6$ in which $R^5$ and $R^6$ are as defined above.

3. A compound of claim 1 wherein
R is hydrogen;
$R^1$ is hydrogen or COY wherein Y is $C_1$-$C_8$alkyl, $C_1$-$C_8$alkoxy or phenyl;
$R^2$ is aryl of 6 carbon atoms;
  substituted aryl or 6 carbon atoms wherein the substituents are $C_1$-$C_8$alkoxy, trifluoromethyl, pentafluoro;
  pyridyl;
  naphthyl;
$R^3$ is $C_1$-$C_8$alkyl or

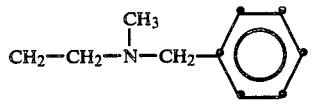

$R^4$ is $C_1$-$C_8$alkyl or aryl of 6 carbon atoms.

4. A compound having the formula:

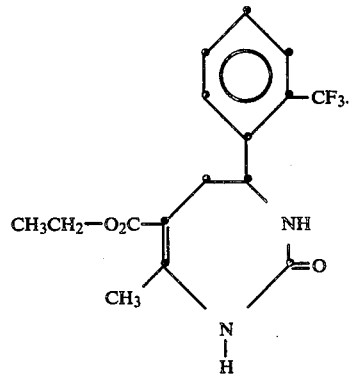

5. A compound having the formula:

6. A compound having the formula:

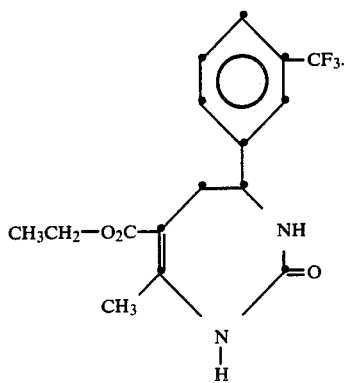

7. A compound having the formula:

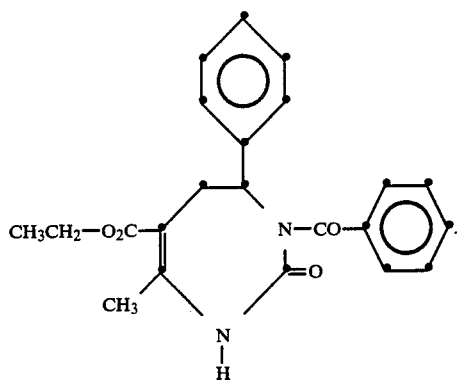

8. A compound having the formula:

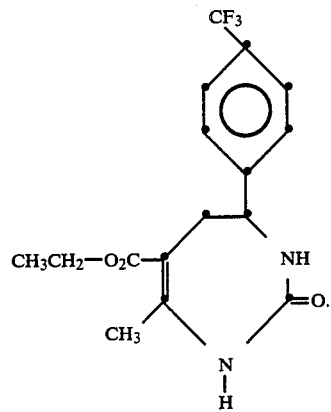

9. A compound having the formula:

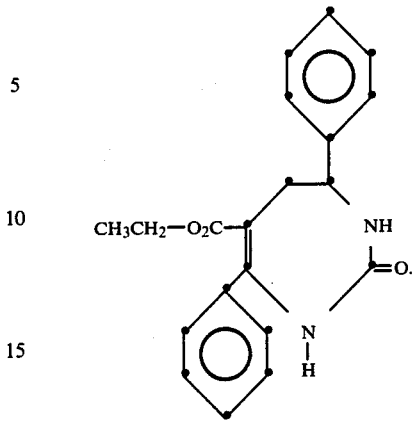

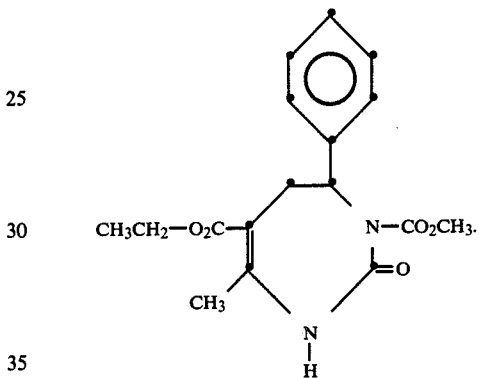

10. A pharmaceutical composition for treating cardiovascular disorders consisting essentially of a pharmaceutically acceptable carrier and a pharmaceutically effective amount of a compound of claim 1.

11. The composition of claim 10 wherein said pharmaceutical composition includes an additional pharmaceutical agent selected from the group consisting of, an angiotensin converting enzyme inhibitor, and antihypertensive, a diurectic, a β-blocker, and a cardiotonic agent as well as admixtures and combinations thereof.

12. The composition of claim 11 wherein said additional pharmaceutical agent is selected from the group: enalapril, hydralazine hydrochloride, hydrochlorothiazide, and timolol.

13. A method for treating cardiovascular disorders comprising administering to a patient in need of such treatment a pharmaceutically effective amount of a compound of claim 1.

14. A process for preparing a compound having the formula:

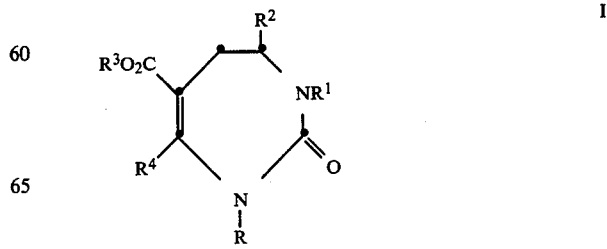

I wherein R–R$^4$ are as defined in claim 1 which comprises:

treating under anhydrous conditions and at reduced temperature, a compound having the formula:

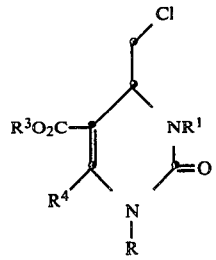

wherein R, R$^1$, R$^3$ and R$^4$ are defined in claim 1, with a magnesium bromide compound having the formula:

R$^2$MgBr wherein R$^2$ is as defined in claim 1, followed by concentration of the reaction product to obtain a compound of formula (I).

* * * * *